United States Patent [19]

Kiel et al.

[11] Patent Number: 5,374,811

[45] Date of Patent: Dec. 20, 1994

[54] BLOOD AND TISSUE REWARMING DEVICE

[75] Inventors: Johnathan L. Kiel; David N. Erwin; David M. Simmons; Christopher McQueen, all of San Antonio, Tex.

[73] Assignee: The United States of America as represented by the Secretary of the Air Force, Washington, D.C.

[21] Appl. No.: 879,015

[22] Filed: May 6, 1992

[51] Int. Cl.$^5$ ............................................. H05B 6/78
[52] U.S. Cl. .................................... 219/753; 219/687; 219/710; 604/114; 604/409
[58] Field of Search ............... 219/10.55 F, 10.55 R, 219/10.55 M, 10.55 A, 400, 745, 687, 752, 753, 754, 755, 710; 128/804; 604/114, 409

[56] References Cited

U.S. PATENT DOCUMENTS

| | | | |
|---|---|---|---|
| 3,427,422 | 2/1969 | Muller | 219/10.55 F |
| 3,462,575 | 8/1969 | Holaday | 219/10.55 F |
| 3,737,608 | 6/1973 | Nagao et al. | 219/10.55 F |
| 4,008,754 | 2/1977 | Kraushaar et al. | 165/2 |
| 4,336,435 | 6/1982 | Kashyap et al. | 219/10.55 F |
| 4,427,866 | 1/1984 | Pauly et al. | 219/10.55 B |
| 4,462,215 | 7/1984 | Kuraoka et al. | 62/78 |
| 4,494,385 | 1/1985 | Kuraoka et al. | 62/306 |
| 4,527,550 | 7/1985 | Ruggera et al. | 128/1.5 |
| 4,652,712 | 3/1987 | Zeipel | 219/10.55 F |
| 4,731,072 | 3/1988 | Aid | 604/408 |
| 4,742,202 | 5/1988 | Campbell et al. | 219/10.55 F |
| 4,801,777 | 1/1989 | Auerbach | 219/10.55 M |
| 4,829,997 | 5/1989 | Douwens et al. | 128/201.13 |
| 4,855,555 | 8/1989 | Adams et al. | 219/10.55 F |
| 4,874,915 | 10/1989 | Harms et al. | 219/10.55 F |
| 4,954,679 | 9/1990 | Harms et al. | 219/10.55 M |
| 5,140,120 | 8/1992 | Kasai et al. | 219/10.55 B |

OTHER PUBLICATIONS

J. L. Keil, L. S. Wong, and D. N. Erwin, Title, Physiological Chemistry & Physics & Medical NMR. 18, 1986, Metabolic Effects of Microwave Radiation & Convection Heating on Human Mononuclear Leukocytes 181–187.
Int. J Hyperthermia, Microwave Radiation Effects on the Thermally Driven Oxidase of Erythrocytes, J. L. Kiel/D. N. Erwin 1986 vol. 2, No. 2 201–212.
J. L. Kiel & D. N. Erwin, Title Amer. Journal of Vet. Research, vol. 47 No. 10 pp. 2155–2160, 1986.
R. D. Luff, C. M. Kessler & W. R. Bell, Title Am J Clin. Pathol, vol. 83, No. 1, 1985.
J. L. Kiel & D. N. Erwin, Physiological Chemistry & Physics & Medical NMR, vol. 16, 1984 pp. 317–323.
A. Checcucci, G. Benelli, M. Duminuco, Gaetani, P. Paoletti, S. Vannini & M. Morfini, Title, Jour of Microwave Power, vol. 18, No. 2, 163–168 1983.
G. Rock, E. S. Tackaberry, J. G. Dunn & S. Kashyap, Title Transfusion, vol. 24, No. 1 pp. 60–65, 1984.

*Primary Examiner*—Geoffrey S. Evans
*Assistant Examiner*—Tu Hoang
*Attorney, Agent, or Firm*—Fredric L. Sinder; Thomas L. Kundert

[57] ABSTRACT

An improved method and apparatus for safely and rapidly rewarming large quantities of frozen or refrigerated blood combines microwave, or radio frequency radiation, heating with a forced air system. Forced air is flowed over units of blood or tissue from those units that will absorb the most microwave energy, generally those units closest to the source of microwave energy, to those units that will absorb the least microwave energy, generally those units furthest from the source of microwave energy. The forced air initially thaws the closest units so that they begin to absorb significant microwave energy. The forced air, preferably chilled, then prevents overheating of those closest units by transferring heat to more distant units, beginning their thawing and contributing to their rewarming. The microwave energy source is turned off when the output temperature of the forced air reaches a preselected temperature and the flow of forced air continues until the output temperature stabilizes. The apparatus includes a separated stack of perforated plates, each plate holding two units, mounted inside a microwave oven. Forced air drives a turbine rotor which rotates the plates while the air leaving the turbine flows down among the stacked plates and out the microwave oven.

17 Claims, 1 Drawing Sheet

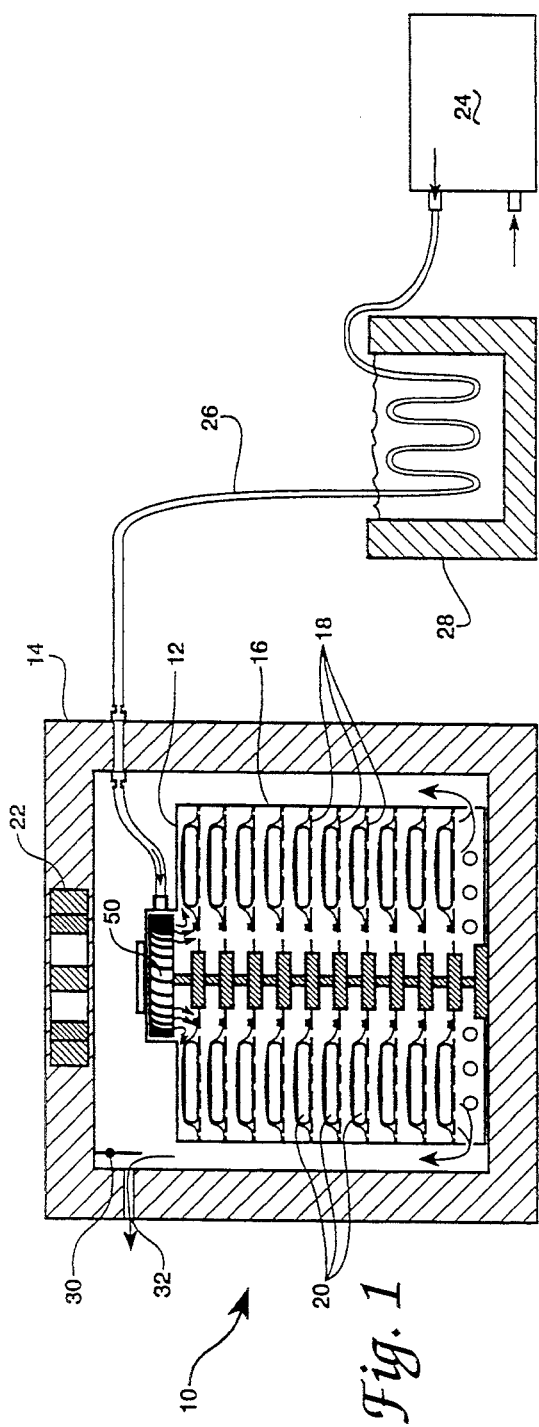
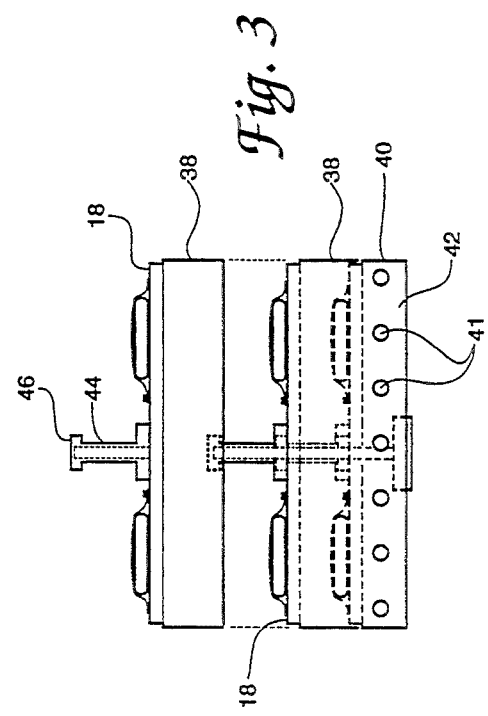
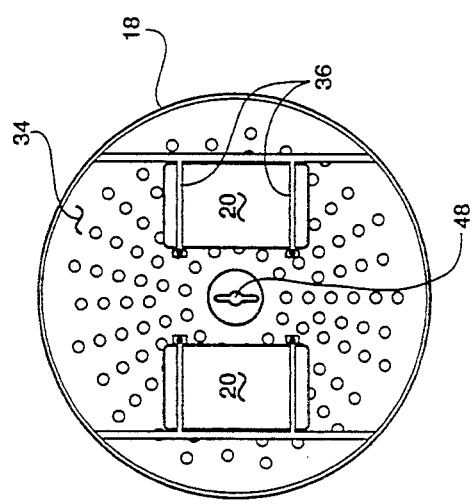

5,374,811

BLOOD AND TISSUE REWARMING DEVICE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to methods and apparatus for rewarming frozen blood and tissue, and more particularly to a combination microwave and forced air apparatus for rapidly, and without damage, rewarming frozen blood and tissue.

Without a safe method for long term storage and later restoration of blood and organs, people will die. Without a fast and high capacity method for restoring stored blood and organs, people may die. The need for rapid rewarming of frozen blood is particularly acute in battlefield hospitals.

Donated blood and organ tissue are generally stored either frozen or refrigerated to maximize safe storage life. They must be thawed and/or rewarmed to normal body temperature before transfusing or transplanting into a patient. Transfusing or transplanting inadequately rewarmed blood or tissue into a patient can cause hypothermia, cardiac arhythmias and coagulopathy.

A number of methods, and implementing apparatus, have been developed in the past to safely rewarm blood and tissue. A useful discussion of that prior art, some of which is repeated or paraphrased in this Background of the Invention, may be found in U.S. Pat. No. 4,801,777 to Auerbach. The Auerbach patent is for a combination microwave and warm water blood rewarming method and apparatus intended to avoid many of the problems of the other prior art microwave or combination microwave and warm water methods.

The most common method for rewarming blood and tissue, particularly for rewarming refrigerated whole blood, is a standard water bath method in which blood is passed through coiled tubing immersed in a temperature-controlled water bath. The problems and difficulties of this unwieldy method are well known in the art and are discussed in the Auerbach patent.

Frozen blood or plasma presents an additional difficulty in that the blood or plasma must first be thawed before it can be rewarmed. The most common method for thawing has been simply to place the plastic blood bags containing the frozen blood or plasma into a warm water bath to thaw, followed by conventional rewarming methods.

Unfortunately, the conventional prior art methods and apparatus for rewarming blood and tissue are generally both slow and can rewarm only small volumes at a time.

Microwave and radiofrequency induction heating have been explored as methods for rewarming blood both faster and in greater volumes. These methods have nob worked well, however, for a variety of reasons. The primary problem has been differential excessive heating, or spot heating, which causes cell damage to whole blood cells. Mechanical agitation and rotation have not solved this problem. A particular problem is that blood inside narrow diameter tubing, an integral part of blood storage bags, frequently overheats and even explodes under microwave heating. Careful monitoring and timing of intermittent microwave energy exposure also has not worked successfully for rewarming whole blood because, among other reasons, of the difficulty of effectively monitoring temperature and time.

Microwave heating has been used slightly more successfully to thaw frozen plasma, which does not have the more prone to damage blood cells of whole blood and packed red cells. Even here, however, the method is complex and unwieldy. The frozen plasma is first softened by placing the bag under warm running water, followed by sealing and removal of all tubing to avoid bursting. The bag is then dried and placed inside a plastic overbag to protect all metal clips and remaining narrow tubulature. Microwave exposure is applied in short (10 second) increments under constant observation until the thaw is completed. At this point, the plasma is only thawed and still must be rewarmed to body temperature.

As mentioned, the primary problem of using microwave heating for thawing and for rewarming blood and tissue is the development of hot spots that leads to cell damage. This is particularly true when dealing with microwave or radiofrequency radiation of frozen material because frozen material is a poor absorber of those energies, increasing the risk of hot spots at the first spot volumes to partially thaw.

Thus it is seen that there is a need for a faster and higher capacity method and apparatus for rewarming blood and tissue, and particularly for thawing and then rewarming frozen blood and tissue.

It is, therefore, a principal object of the present invention to provide an apparatus and method for thawing and rewarming blood and tissue that takes advantage of the speed and capacity advantages offered by microwave radiation heating.

It is another object of the present invention to provide microwave radiation heating of frozen blood and tissue without the usual localized overheating or underheating associated with microwave heating.

It is a feature of the present invention that it uses forced air instead of a water bath to remove and distribute excess heat.

It is another feature of the present invention that its microwave radiation is more continuous, or less intermittent, than prior art systems and is thus faster.

It is an advantage of the present invention that its steady-state microwave irradiation is less injurious to red blood cells.

It is another advantage of the present invention that its forced air system is less bulky than water bath systems.

It is also an advantage of the present invention that it is straightforward and easy to use.

These and other objects, features and advantages of the present invention will become apparent as the description of certain representative embodiments proceeds.

SUMMARY OF THE INVENTION

The present invention provides a fast and safe apparatus and method for thawing and rewarming frozen blood and tissue. The unique discovery of the present invention is that the many advantages of microwave, or radio frequency, radiation heating, particularly its speed, can be obtained without the disadvantage of cell damage from spot overheating, and without bulky water baths, by combining microwave heating with a forced air system, particularly in a novel multi-unit holder and forced air system that first partially thaws with forced air those frozen blood storage bags, or other storage units of frozen blood or tissue, that will be absorbing the most microwave energy, generally as a result of being closest to the source of microwave energy, then, after turning on the microwave energy source, transfers heat from those closest blood storage bags to more distant blood storage bags to prevent overheating of the closest blood storage bags, begin thawing the more distant blood storage bags, and provide more uniform heating.

Accordingly, the present invention is directed to a method for rewarming units of frozen or refrigerated blood or tissue, comprising the steps of providing a source of rf radiation; providing a source of forced air; providing a holder for a plurality of units of frozen or refrigerated blood or tissue; and, flowing forced air over the units from over the units absorbing the most rf radiation energy to over the units absorbing the least rf radiation energy. The method may include measuring the temperature of the forced air at a preselected point; turning off the source of rf radiation after the measured temperature of the forced air reaches a preselected value; and, continuing to flow forced air over the units until the measured temperature of the forced air reaches a preselected value. The source of rf radiation may initially be turned off and turned on after beginning the flowing of forced air. The step of continuing to flow forced air over the units until the measured temperature of the forced air reaches a preselected value may be characterized as continuing to flow forced air over the units until the measured temperature of the forced air becomes constant. The holder may comprise a plurality of holders arranged so that some units are held closer to the source of rf radiation than others and the forced air is flowed over the units from over the units closest to the source of rf radiation to over the units most distant from the source of rf radiation. The temperature of the forced air may be measured after having passed over the most distant units. The units may be initially frozen, the source of forced air may initially provide air at room temperature to begin thawing the units closest to the source of rf radiation; and, the source of forced air may later provide air at a cooler temperature to prevent the units closest to the source of rf radiation from overheating. The source of rf radiation may be initially turned off and not turned on until the units closest to the source of rf radiation begin to thaw.

The present invention is also directed to an apparatus for rewarming units of frozen or refrigerated blood or tissue, comprising means for supplying rf radiation; means for supplying forced air; means for holding a plurality of units of frozen or refrigerated blood or tissue wherein some units are held closer to the source of rf radiation than others; and, means for directing the forced air from over the units closest to the means for supplying rf radiation to over the units most distant from the means for supplying rf radiation. The apparatus may further comprise means for measuring the output temperature of the forced air after having passed over the most distant units. The apparatus may additionally comprise means for turning off the means for supplying rf radiation when the output temperature of the forced air reaches a preselected value. The apparatus may still further comprise means for cooling the forced air; and, means for beginning the cooling of the forced air on the happening of a preselected event. The plurality of holders may comprise a plurality of perforated stacked plates arranged coaxially in a spaced relationship, wherein each plate can hold a plurality of the units of frozen or refrigerated blood or tissue. The apparatus may additionally comprise means for rotating the stacked plates. The means for rotating the stacked plates may comprise a turbine operatively interconnected with the stacked plates and means for directing forced air against the turbine. The means for rotating the stacked plates may comprise means for interlocking the stacked plates so that they rotate together. Each plate may comprise a top, a bottom and circumferential sides extending mostly perpendicularly away from the bottom of each plate, whereby the outside edge of each circumferential side can fit over the top of an adjacent plate to block the flow of forced air around the plates and direct the flow of forced air through the plates. At least one plate may have perforations in its circumferential side so that the forced air can escape through those perforations.

DESCRIPTION OF THE DRAWINGS

The present invention will be more clearly understood from a reading of the following detailed description in conjunction with the accompanying drawings wherein:

FIG. 1 is a cross-sectional view of a blood and tissue rewarming apparatus according to the teachings of the present invention showing a stack of rotating perforated plates for holding blood storage bags inside a microwave oven;

FIG. 2 is a top-down view of a single perforated plate from the middle of the stack of FIG. 1; and, FIG. 3 is a phantom side view of the bottom three of the stack of perforated plates of FIG. 1 shown removed from the microwave oven.

DETAILED DESCRIPTION

Referring now to FIG. 1 of the drawings, there is shown a cross-sectional view of a blood and tissue rewarming apparatus, or rewarmer, 10 according to the teachings of the present invention. Rewarmer 10 primarily comprises a multi-unit blood or tissue sample holder 12 that sits inside a microwave oven 14. Holder 12 comprises a stack 16 of interlocking perforated plates 18. Each plate 18 holds two units 20 of frozen or refrigerated blood or tissue. A magnatron or rf energy source 22 is located on the top of microwave oven 14. Forced, or pressurized, air is supplied to rewarmer 10 from a forced air supply 24 through tubing 26. Tubing 26 passes through a coolant bath 28 between forced air supply 24 and rewarmer 10. An electromagnetically nonperturbing electrothermia probe 30 measures the temperature of forced air escaping oven 14 through an outlet 32.

FIGS. 2 and 3 show plates 18 in greater detail. FIG. 2 is a top-down view of a single perforated plate from the middle of stack 16. FIG. 3 is a phantom side view of the bottom three plates 18 of stack 16. Each plate 18 includes a perforated disc section 34 to allow forced air to pass through stack 16 from top to bottom. Elastic straps 36 secure a pair of units 20 to each plate 18. Each plate also includes a circumferential side 38 extending perpendicularly downward from the bottom off each disc section 34. Sides 38 fit over each lower plate to restrict the flow of forced air to within stack 16. A bottom plate 40 has holes 41 along its side 42 to allow forced air to leave stack 16. Forced air, after leaving stack 16, escapes oven 14 through outlet 32.

Plates 18 interlock one to the other through a post 44, key 46 and lock 48 arrangement so that they will rotate together. The topmost plate 18 interlocks with a turbine rotor 50 so that rotation of rotor 50 will cause rotation of the entire stack 16.

In use with frozen units 20 of blood or tissue, forced air, preferably initially at room temperature, is introduced through tube 26 to impinge on rotor 50 so that rotor 50, and interlocked stack 16, begins to rotate. As the forced air begins to flow down through stack 16 and over the units 20 closest to magnatron 22, those units begin to thaw so that rf radiation can more efficiently begin to heat the thawed parts of those closest units 20. The forced air is then chilled by passing tubing 26 through coolant bath 28 so that the incoming chilled air transfers heat from the thawed parts of those closest units 20 to keep them from overheating. The now slightly warmed forced air begins to thaw units 20 below those closest units 20 so that those further units 20 will also begin to absorb rf radiation energy. The temperature of the forced air increases as rf radiation continues to heat units 20 until the temperature of the forced air reaches a preselected level measured at probe 30 indicating that closest units 20 have reached a maximum safe temperature. At this point, rf radiation source 22 is shut off, either manually or automatically, and the forced air flow continued until the air temperature at probe 30 either reaches a preselected temperature or stabilizes. As the forced air flow continues, its temperature measured at probe 30 will fall as the rate of heat transfer from the warmer units 20 nearer rf radiation source 22 to cooler units further away from rf radiation source 22 increases and the temperature of all units 20 finally reaches a uniform temperature.

In use with refrigerated units 20 of blood or tissue, the operation of rewarmer 10 is largely unchanged. The forced air still prevents overheating of units 20 closest to rf radiation source 22 and transfers that heat to units 20 more distant from rf radiation source 22.

The ideal terminal temperature of the units will be 37° C. Because the chilled temperature of the forced air will typically have to be below 37° C. to maintain rf radiation heating for as long as possible without overheating the units 20 closest to the rf radiation source, the forced air flow may have to be shut off at a point before all units 20 reach a uniform temperature so that heat transfer by convection completes temperature stabilization of all the units at a higher terminal temperature. Rewarmers 10 can be calibrated with saline-filled phantoms of blood and tissue containers with nonperturbing electrothermia probes inside the containers to determine the parameters of rf power levels, air flow rate, exposure times, and so forth for different numbers of both frozen and refrigerated containers.

In tests using combined forced air and microwave radiation to rewarm refrigerated other biological materials, improvements in heating times of almost 80 times over heating in an incubator were observed.

Those with skill in the art will see that the operation of the disclosed apparatus may be simplified by a variety of different methods without changing the underlying combination forced air and rf radiation method. For example, the temperature of the forced air may be dynamically varied. The forced air may be initially warmed to more quickly begin thawing the units 20 closest to rf radiation source 22, then chilled to prevent overheating and to transfer heat to further units 20 after rf radiation source 22 is turned on, followed by gradual rewarming to bring all units 20 to a preselected uniform terminal temperature. The advantage of not attempting to dynamically vary the temperature of the forced air, and even to use chilled air (which will still initiate thawing) from the beginning of the process is that it greatly simplifies the apparatus. For example, the presently envisioned preferred embodiment can use the coolant and coolant package in which frozen blood is transported for the coolant bath 28.

The operation of the disclosed apparatus may be also be changed by dynamically varying the output power of the rf radiation generator, by pulsing its output, or by starting and stopping it at different times.

The preferred embodiment for a simple apparatus incorporating the teachings of the present invention will use a conventional 2450 MHz microwave oven. The perforated plates should be constructed of microwave transparent plastics such as polystyrene, TEFLON, polypropylene, or the like. To accommodate conventional size frozen blood containers (18×14×4.5 cm), the minimum plate size should be 31 cm in diameter and the minimum spacing between plates should be 6 cm. The size of the oven should be selected as the smallest size into which the stack holder will fit.

The stack holder may be placed inside a wave guide instead of a microwave oven. The radiation pattern inside a waveguide may be more uniform than that generated inside a microwave oven. Generally, however, some blood or tissue containers will always be positioned so that they absorb more rf radiation energy than others. The direction of the air flow should always be from those containers that will, for whatever reason, absorb more rf radiation energy, to those containers that will absorb the least. The frequency of the radiation generated by a waveguide, or by a microwave oven, may be in the range of 900 MHz to 3 GHz and may be pulsed.

The plates may be stacked so that the blood or tissue containers are not vertically aligned, but are offset forming a spiral. This configuration will allow for better microwave distribution and air flow.

Instead of an externally placed air compressor, a fan may be mounted inside the oven where it can draw air into the oven from the outside, circulate it within the oven, and then exhaust it to the outside.

The disclosed method and apparatus for rewarming blood and tissue successfully demonstrates the use of a combination forced air and microwave method to safely rewarm blood and tissue at speeds and in quantities much greater than has been possible in the prior art. Although the disclosed apparatus and method is specialized, its teachings will find application in other areas where rapid thawing and rewarming of materials are desired.

As used in the following claims, the term "closest to the source of rf radiation," or similar terms, will be understood by those with ordinary skill in the art as meaning functionally closer so that, for example, if a magnatron were mounted in the top of a microwave oven, but the microwaves from the magnatron were directed through a waveguide or similar apparatus to emerge upwards from the bottom of the microwave oven, "closest to the source of rf radiation" would mean, in that example, closest to the bottom of the microwave oven.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

We claim:

1. A method for rewarming units of frozen or refrigerated blood or tissue, comprising the steps of:
   (a) providing a source of rf radiation;
   (b) providing a source of forced air;
   (c) providing a rotatable support having a plurality of holders for supporting the units of frozen or refrigerated blood or tissue, wherein the distance between said source of rf radiation and each of said units does not vary as each of said holders rotates and the holders are arranged so that at least one of the units is supported at all times during operation of the method closer to the source of rf radiation than the others; and,
   (d) flowing forced air over the units from the at least one unit closest to the source of rf radiation to over the units most distant from the source of rf radiation.

2. The method for rewarming units of frozen or refrigerated blood or tissue according to claim 1, further comprising the steps of:
   (a) measuring the temperature of the forced air at a preselected point;
   (b) turning off the source of rf radiation after the measured temperature of the forced air reaches a first preselected value; and,
   (c) continuing to flow forced air over the units until the measured temperature of the forced air reaches a second preselected value.

3. The method for rewarming units of frozen or refrigerated blood or tissue according to claim 2, wherein the source of rf radiation is initially turned off and is turned on after beginning the flowing of forced air.

4. The method for rewarming units of frozen or refrigerated blood or tissue according to claim 2, wherein step (c) is characterized as continuing to flow forced air over the units until the measured temperature of the forced air becomes constant.

5. A method for rewarming units of frozen or refrigerated blood or tissue, comprising the steps of:
   (a) providing a source of rf radiation;
   (b) providing a source of forced air;
   (c) providing a plurality of holders for supporting the units of frozen or refrigerated blood or tissue wherein the holders are arranged so that at least one of the units is supported closer to the source of rf radiation than the others;
   (d) flowing forced air over the units from the at least one unit closest to the source of rf radiation to over the units most distant from the source of rf radiation; and,
   (e) wherein the temperature of the forced air is measured after having passed over the units most distant from the source of rf radiation.

6. The method for rewarming units of frozen or refrigerated blood or tissue according to claim 1, wherein:
   (a) the units are initially frozen;
   (b) the source of forced air initially provides air at room temperature to begin thawing the units closest to the source of rf radiation; and,
   (c) the source of forced air later provides air at a cooler temperature to prevent the units closest to the source of rf radiation from overheating.

7. The method for rewarming units of frozen or refrigerated blood or tissue according to claim 1, wherein:
   (a) the units are initially frozen; and,
   (b) the source of rf radiation is initially turned off and is not turned on until the units closest to the source of rf radiation begin to thaw.

8. An apparatus for rewarming units of frozen or refrigerated blood or tissue, comprising:
   (a) a source of rf radiation;
   (b) a source of forced air;
   (c) a rotatable support having a plurality of holders for supporting the units of frozen or refrigerated blood or tissue wherein the distance between said source of rf radiation and each of said units does not vary as each of said holders rotates and at least one of the units is supported at all times during operation of the apparatus closer to the source of rf radiation than others; and,
   (d) air directors for directing the forced air from over the at least one unit closest to the source of rf radiation to over the units most distant from the source of rf radiation.

9. The apparatus for rewarming units of frozen or refrigerated blood or tissue according to claim 8, further comprising:
   (a) a cooler for cooling the forced air; and
   (c) a controller for beginning the cooling of the forced air.

10. An apparatus for rewarming units of frozen or refrigerated blood or tissue, comprising:
    (a) a source of rf radiation;
    (b) a source of forced air;
    (c) holders for supporting a plurality of the units of frozen or refrigerated blood or tissue wherein at least one of the units is supported closer to the source of rf radiation than others;
    (d) air directors for directing the forced air from over the at least one unit closest to the source of rf radiation to over the units most distant from the source of rf radiation; and,
    (e) a temperature measuring probe for measuring the temperature of the forced air after the forced air has passed over the units most distant from the source of rf radiation.

11. The apparatus for rewarming units of frozen or refrigerated blood or tissue according to claim 10, further comprising a controller for turning off the source of rf radiation when the output temperature of the forced air reaches a preselected value.

12. An apparatus for rewarming units of frozen or refrigerated blood or tissue, comprising:
    (a) a source of rf radiation;
    (b) a source of forced air;
    (c) holders for supporting a plurality of the units of frozen or refrigerated blood or tissue wherein at least one of the units is supported closer to the source of rf radiation than others;
    (d) air directors for directing the forced air from over the units closest to the source of rf radiation to over the units most distant from the source of rf radiation; and,
    (e) wherein the holders for supporting a plurality of the units of frozen or refrigerated blood or tissue comprise a plurality of perforated stacked plates arranged coaxially in a spaced relationship.

13. The apparatus for rewarming units of frozen or refrigerated blood or tissue according to claim 12, further comprising a rotator for turning the stacked plates.

14. The apparatus for rewarming units of frozen or refrigerated blood or tissue according to claim 13, wherein the rotator for turning the stacked plates comprises:
(a) a turbine operatively interconnected with the stacked plates; and,
(b) an air director for directing forced air against the turbine.

15. The apparatus for rewarming units of frozen or refrigerated blood or tissue according to claim 13, wherein the rotator for turning the stacked plates further comprises interlocks for interlocking the stacked plates so that they turn together.

16. The apparatus for rewarming units of frozen or refrigerated blood or tissue according to claim 14, wherein at least one of the stacked plates has perforations in its circumferential side so that the forced air escapes through those perforations.

17. The apparatus for rewarming units of frozen or refrigerated blood or tissue according to claim 12, wherein each stacked plate further comprises a top, a bottom, and a circumferential side extending perpendicularly away from the bottom of each stacked plate, the circumferential side having an outside edge, whereby the outside edge of each circumferential side fits over the top of an adjacent plate to block the flow of forced air around the stacked plates and direct the flow of forced air through the stacked plates.

* * * * *